United States Patent
Zhang et al.

(10) Patent No.: US 11,116,806 B2
(45) Date of Patent: Sep. 14, 2021

(54) COMPOSITE PROBIOTIC LACTIC ACID BACTERIA POWDER AND PREPARATION METHOD AND USE THEREOF

(71) Applicant: BEIJING SCITOP BIO-TECH CO., LTD, Beijing (CN)

(72) Inventors: Jianjun Zhang, Beijing (CN); Chen Ma, Beijing (CN); Jicheng Wang, Beijing (CN)

(73) Assignee: BEIJING SCITOP BIO-TECH CO., LTD., Beijing (CN)

( * ) Notice: Subject to any disclaimer, the term of this patent is extended or adjusted under 35 U.S.C. 154(b) by 116 days.

(21) Appl. No.: 16/249,156

(22) Filed: Jan. 16, 2019

(65) Prior Publication Data
US 2019/0216866 A1 Jul. 18, 2019

(30) Foreign Application Priority Data
Jan. 18, 2018 (CN) .......................... 201810049205.7

(51) Int. Cl.
| | | |
|---|---|---|
| A61K 35/747 | (2015.01) | |
| A61K 35/745 | (2015.01) | |
| A61K 9/14 | (2006.01) | |
| A61K 31/702 | (2006.01) | |
| A61P 31/00 | (2006.01) | |
| A61K 36/45 | (2006.01) | |
| A61K 36/73 | (2006.01) | |
| A61P 1/00 | (2006.01) | |
| A61P 11/00 | (2006.01) | |
| A61K 31/716 | (2006.01) | |
| A61K 9/00 | (2006.01) | |

(52) U.S. Cl.
CPC .......... *A61K 35/747* (2013.01); *A61K 9/0095* (2013.01); *A61K 9/14* (2013.01); *A61K 31/702* (2013.01); *A61K 31/716* (2013.01); *A61K 35/745* (2013.01); *A61K 36/45* (2013.01); *A61K 36/73* (2013.01); *A61P 1/00* (2018.01); *A61P 11/00* (2018.01); *A61P 31/00* (2018.01)

(58) Field of Classification Search
None
See application file for complete search history.

(56) References Cited

U.S. PATENT DOCUMENTS

| | | | |
|---|---|---|---|
| 9,084,434 B2 * | 7/2015 | Hodal, Jr. | .............. A61K 47/26 |
| 2012/0107395 A1 | 5/2012 | Xie et al. | |

FOREIGN PATENT DOCUMENTS

| | | | |
|---|---|---|---|
| CN | 104605277 A | | 5/2015 |
| CN | 107058158 | * | 8/2017 |
| CN | 107058158 A | | 8/2017 |

OTHER PUBLICATIONS

Wenyi Zhang et. al; Short communication: Single molecule, real-time sequencing technology revealed species—and strain-specific methylation patterns of 2 Lactobacillus strains; J. Dairy Sci. 98 :3020-3024; American Dairy Science Association, 2015.

Lifeng Wang; Effect of oral consumption of probiotic Lactobacillus planatarum P-8 on fecal microbiota, SIgA, SCFAs and TBAs of adults of different ages; Nutrition 30(2014) 776-783.

Yang Ying; Probiotic Characteristic of Lactobacillus planatarum HO-69 applied in a oral cavity; West China Journal of Stomatology vol. 26 No. 5 Oct. 2008.

* cited by examiner

*Primary Examiner* — Vera Afremova
(74) *Attorney, Agent, or Firm* — Reising Ethington, P.C.

(57) ABSTRACT

Provided are a composite probiotic lactic acid bacteria powder and a preparation method and use thereof, the composite probiotic lactic acid bacteria powder can be composited from *Lactobacillus casei* Zhang bacteria powder, *Bifidobacterium animalis* V9 bacteria powder, *Lactobacillus plantarum* P8 bacteria powder, *Lactobacillus plantarum* C2 bacteria powder, with prebiotics and fruit-vegetable powder. The composite probiotic lactic acid bacteria powder has a significantly protective effect against irritable bowel syndrome, oral infection and nasal cavity infection, and can prevent the occurrence of upper respiratory tract infection, at the same time, it can improve gastrointestinal symptoms, regulate gut microbiota and improve the body's immunity.

11 Claims, 5 Drawing Sheets

Number of days when respiratory inflammation occurred in every month during a period of 12 months; aged over 50

Occurrence number of diarrhea in every month during a period of 12 months; aged 20-50

COMPOSITE PROBIOTIC LACTIC ACID BACTERIA POWDER AND PREPARATION METHOD AND USE THEREOF

FIELD OF TECHNOLOGY

The present invention belongs to the field of biotechnology, and particularly relates to a composite probiotic lactic acid bacteria powder and a preparation method and use thereof.

BACKGROUND

Intestinal tract, which is the largest digestive organ in human body, plays an important role in food digestion and nutrient absorption in the body. Over the past 15 years, with rapid development of high-throughput sequencing technologies and in-depth studies on the intestinal tract, the term "gut microbiota" appears more and more frequently in people's sights. The gut microbiota has been regarded as another important organ in the human body. The human gut microbiota adheres to the nutrient-rich intestinal tract and plays an important role in the metabolism of food, the provision of energy and nutrients, the inhibition of the growth of pathogenic microorganisms and the like in host. At the birth of the host, gut microbiota has been formed. From beginning of the early growth and development of the host, the gut microbiota participates in formation of the metabolism, immunology and cognitive development of the host. As the host grows into early childhood, the composition of the gut microbiota reaches a stable state, and is in a dynamic balance with the health of the host. Dysbacteriosis is harmful to the health of the host, resulting into various physical discomforts or diseases, such as gastrointestinal discomfort, obesity, diabetes, cardiovascular disease, inflammatory bowel disease and the like.

Irritable bowel syndrome (IBS) is a clinical common chronic intestinal disease characterized by intermittent abdominal pain, and abdominal distension with changes in stool traits and/or bowel habits and without intestinal morphological changes. According to patient's stool traits, this disease can be divided into three types: constipation type, diarrhea type, and constipation and diarrhea alternating type. The symptoms of the disease are recurrent, which not only brings pains to patients but also affects patients' quality of life. Due to repeated attacks and medical treatment, many medical resources are consumed, bringing a heavy social and economic burden. However, the pathogenesis and mechanism of the disease are not fully understood yet, and thus symptomatic treatments are often used in clinical practice. In recent years, studies have found that the gut microbiota of patients with irritable bowel syndrome shows a variation, in which the ratio of the amount of *Firmicutes* bacteria (including *Ruminococcus, Clostridium, Proteobacteria, Escherichia Coli, Enterococcus, Enterobacter, Prevotella,* and *Dorea*) to the amount of *Bacteroidetes* bacteria is increased, and the diversity of the gut microbiota is reduced with a decreased number of beneficial bacteria, such as *Bifidobacterium, Lactobacillus, Bacteroides* and *Faecalibacterium*. From the perspective of regulating the gut microbiota, the treatment with probiotics has made significant progresses in recent years, but the efficacy varies depending on strains and contents of probiotics. Therefore, there is an urgent need for a highly effective and safe product to alleviate symptoms of the patients.

SUMMARY

To solve the above technical problems, there is provided a composite probiotic lactic acid bacteria powder, and a preparation method and use thereof.

In order to achieve the above objectives, a first aspect provides a composite probiotic lactic acid bacteria powder comprising *Lactobacillus plantarum* C2 with an accession number of CGMCC No. 14532, *Lactobacillus casei, Lactobacillus plantarum* and *Bifidobacterium animalis.*

In combination with the first aspect, in a first possible embodiment of the first aspect, the effective viable count of *Lactobacillus plantarum* C2 is greater than or equal to $1.0 \times 10^9$ CFU/g, the effective viable count of *Lactobacillus casei* is greater than or equal to $3.0 \times 10^9$ CFU/g, the effective viable count of *Lactobacillus plantarum* is greater than or equal to $3.0 \times 10^9$ CFU/g, and the effective viable count of *Bifidobacterium animalis* is greater than or equal to $4.0 \times 10^9$ CFU/g.

In combination with the first possible embodiment of the first aspect, in a second possible embodiment of the first aspect, the total effective viable count of the composite probiotic lactic acid bacteria powder is greater than or equal to $1 \times 10^{10}$ CFU/g, preferably is $1.6 \times 10^{10}$ CFU/g.

In combination with the second possible embodiment of the first aspect, in a third possible embodiment of the first aspect, the composite probiotic lactic acid bacteria powder further comprises prebiotics and/or fruit-vegetable powder, wherein, the prebiotics comprise one or more of fructo-oligosaccharide, galacto-oligosaccharide, xylo-oligosaccharide, isomalto-oligosaccharide, oligolactose, oligochitosan, soybean oligosaccharide, inulin, and polydextrose; and the fruit-vegetable powder comprises one or more of blueberry powder, strawberry powder, cranberry powder, cherry powder, apple powder, banana powder, papaya powder, mango powder, pitaya powder, pumpkin powder, carrot powder, grape powder, pomegranate powder, Hami cantaloupe powder, Chinese wolfberry powder, red jujube powder, and kiwifruit powder.

The fruit-vegetable powder is a powdered product prepared by subjecting fresh fruits and vegetables to processes such as spray drying or freeze drying. The abundant proteins, unsaturated fatty acids, dietary fibers, various minerals and natural vitamins in the fruit-vegetable powder can provide diverse nutrients for the body and endow a good flavor to the composite probiotic lactic acid bacteria powder at the same time. Prebiotics are indigestible food ingredients and dietary supplements having a beneficial effect on the host by selectively stimulating the growth and activity of bacteria in one kind of or a few kinds of colonies, and thereby improving the health of the host. Prebiotics are nourishments of probiotic lactic acid bacteria. Coadministration of prebiotics with probiotic lactic acid bacteria can promote the growth and colonization of strains, thereby giving better probiotic effect.

In a fourth possible embodiment of the first aspect, the *Lactobacillus casei* is *Lactobacillus casei* Zhang with an accession number of CGMCC No. 5469; the *Lactobacillus plantarum* is *Lactobacillus plantarum* P8 with an accession number of CGMCC No. 6312; and the *Bifidobacterium animalis* is *Bifidobacterium animalis* V9 with an accession number of CGMCC No. 5470.

In a fifth possible embodiment of the first aspect, the composite probiotic lactic acid bacteria powder comprises 1-6 parts by weight of *Lactobacillus plantarum* C2 bacteria powder, 0.1-8 parts by weight of *Lactobacillus casei* Zhang bacteria powder, 0.1-6 parts by weight of *Lactobacillus plantarum* P8 bacteria powder, 0.1-8 parts by weight of *Bifidobacterium animalis* V9 bacteria powder, 30-75 parts by weight of prebiotics, and 5-35 parts by weight of fruit-vegetable powder.

In a sixth possible embodiment of the first aspect, the composite probiotic lactic acid bacteria powder has a moisture content of not more than 2%.

In a second aspect, the invention further provides use of the above composite probiotic lactic acid bacteria powder in the preparation of a product for treating irritable bowel syndrome, upper respiratory tract infection, oral infection, and nasal cavity infection.

One or more embodiments described herein may have the following beneficial effects.

1. The composite probiotic lactic acid bacteria powder can be composited from *Lactobacillus plantarum* C2, *Lactobacillus casei* Zhang, *Lactobacillus plantarum* P8 and *Bifidobacterium animalis* V9. The four bacterial powders have good acid resistance, artificial gastric juice and artificial digestive juice tolerance, and bile salt tolerance, and have no drug-resistant plasmid. The use of the composite probiotic lactic acid powder in the treatment of patients with irritable bowel syndrome provides a safe and effective method for the treatment of irritable bowel syndrome, which relieves the symptoms of patients, improves their quality of life, and saves social and medical resources.

2. The composite probiotic lactic acid bacteria powder can be effective in treating irritable bowel syndrome, has a significantly protective effect against oral infection and nasal cavity infection, and can prevent the occurrence of upper respiratory tract infection, and simultaneously, it can improve gastrointestinal symptoms, regulate gut microbiota and improve the body's immunity.

DESCRIPTION OF THE EMBODIMENTS

Figure 1:
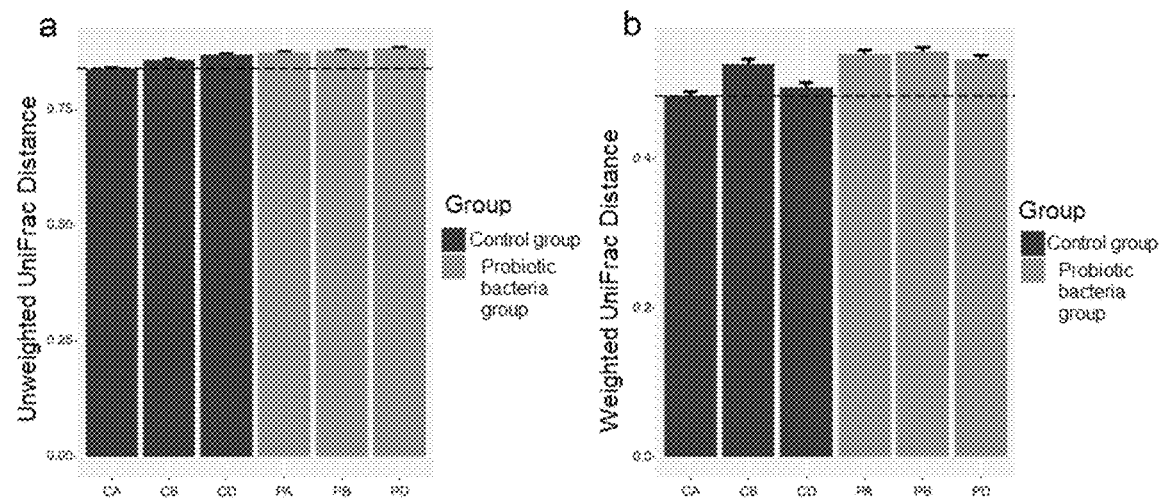
FIG. 1 shows comparison views of Unweighted UniFrac distance and weighted UniFrac distance of samples between the control group and the composite probiotic lactic acid bacteria powder group.

One or more embodiments of the invention are explained below in combination with Examples which are merely illustrative. Unless otherwise stated, the technical means used are all methods known to those skilled in the art. In addition, embodiments are to be regarded as illustrative rather than limiting the scope of the invention(s). The essence and scope of the invention are defined only by the claims. It will be apparent to those skilled in the art that various changes and modifications can be made to the composition and amount of materials in the embodiments without departing from the spirit and scope of the invention.

The *Lactobacillus plantarum* C2 used in the following Examples was deposited on Aug. 18, 2017 at the China General Microbiological Culture Collection Center (CGMCC), the accession number is CGMCC No. 14532, the address of the CGMCC is Institute of Microbiology, Chinese Academy of Sciences, No. 1 West Beichen Road, Chaoyang District, Beijing, 100101, China, and this strain is classified as *Lactobacillus plantarum*. The strain is a lactic acid bacteria strain with excellent probiotic characteristics, which was isolated and screened from naturally fermented pickle in Sichuan Province (China) in 2012. Acids can be quickly produced in the crops or animal wastes fermented by the strain so as to control the pH value of the materials, in which a high-yield organic acid with broad-spectrum inhibition effect on the growth and reproduction of *Escherichia coli* pathogens and moulds is 4-hydroxyphenyl lactic acid. This organic acid was first discovered by the team of the invention and has high research potential.

The *Lactobacillus plantarum* P8 was deposited on Jun. 28, 2012 at the China General Microbiological Culture Collection Center (CGMCC), the accession number is CGMCC No. 6312, the address of the CGMCC is Institute of Microbiology, Chinese Academy of Sciences, No. 1 West Beichen Road, Chaoyang District, Beijing, 100101, China, and this strain is classified as *Lactobacillus plantarum*. This strain is a lactic acid bacteria strain with excellent probiotic characteristics, which was isolated and screened from naturally fermented yogurt in a nomad family in Inner Mongolia Autonomous Region (China) in 2003. Researches were performed using in vitro experiments, animal models and human experiments to systematically evaluate probiotic functions of the strain, and the probiotic mechanism of the strain was further analyzed by genomics means. At present, it is proved that the strain has excellent endurance against gastrointestinal digestive juice, and can colonize and reproduce in the intestinal tracts of humans and animals, improve gut microbiota, regulate blood lipid metabolism, protect and repair liver, and improve immunity of the body. This strain has been disclosed in a Chinese patent for invention titled "Use of *Lactobacillus plantarum* strain in improving alcoholic liver damage" with a publication No. 102994422A.

The *Lactobacillus casei* Zhang was deposited on Nov. 18, 2011 at the China General Microbiological Culture Collection Center (CGMCC), the accession number is CGMCC No. 5469, the address of the CGMCC is Institute of Microbiology, Chinese Academy of Sciences, No. 1 West Beichen Road, Chaoyang District, Beijing, 100101, China, and this strain is classified as *Lactobacillus casei*. This strain has been disclosed in a Chinese patent for invention titled "*Lactobacillus casei* strain for converting isoflavones during soymilk fermentation" with a publication No. 102851222A.

The *Bifidobacterium animalis* V9 was deposited on Nov. 18, 2011 at the China General Microbiological Culture Collection Center (CGMCC), the accession number is CGMCC No. 5470, the address of the CGMCC is Institute of Microbiology, Chinese Academy of Sciences, No. 1 West Beichen Road, Chaoyang District, Beijing, 100101, China, and this strain is classified as *Bifidobacterium animalis* subsp *lactis*. This strain has been disclosed in a Chinese patent for invention titled "*Lactobacillus casei*, *Bifidobacterium animalis*, *Lactobacillus plantarum* and *Bacillus subtilis* for probiotics solid fermentation of feed additive" with a publication No. 103421711A.

Example 1: Composite Probiotic Lactic Acid Bacteria Powder with a Blueberry Flavor A method for preparing *Lactobacillus plantarum* C2 bacteria powder, *Lactobacillus casei* Zhang bacteria powder, *Lactobacillus plantarum* P8 bacteria powder and *Bifidobacterium animalis* V9 bacteria powder, comprised the following steps:

(1) four fermentation strains (strains of *Lactobacillus plantarum* C2, *Lactobacillus casei* Zhang, *Lactobacillus plantarum* P8 and *Bifidobacterium animalis* V9) were respectively subjected to high-density fermentation: one loop of slant bacteria culture of activated *Lactobacillus plantarum* C2, *Lactobacillus* genus Zhang, *Lactobacillus plantarum* P8, and *Bifidobacterium animalis* V9 was respectively taken, and individually inoculated into MRS medium and cultured for 18-24 hours at a same temperature in the range of 33-37° C. and a same rotation speed in the range of 50-100 rpm, giving primary seed liquids respectively;

(2) the cultured primary seed liquids were transplanted to MRS medium again for secondary activation with an inoculation amount in the range of 3%-10% (v/v), and secondary seed liquids were obtained after an activation time of 18-24 hours, respectively;

(3) the secondary seed liquids were separately added to different fermenter media with a same inoculation amount in the range of 3%-10% (v/v), under the conditions of a same fermentation temperature in the range of 33-37° C., a same rotation speed in the range of 50-100 rpm and a same ventilation rate in the range of 0.3-1 L/min; the fermentation process, throughout which the pH of the respective fermentation broth was adjusted to a same pH value in the range of 5.6-6.2, was carried out for 8-12 hours to give final fermentation broths of *Lactobacillus plantarum* C2, *Lactobacillus casei* Zhang, *Lactobacillus plantarum* P8 and *Bifidobacterium animalis* V9, respectively, and the resultant final broths were centrifuged at 5000-12000 rpm for 5-15 minutes to collect bacterial cells, respectively;

the fermenter medium comprises the following components (g/L): 50-80 g/L of sucrose, 20-40 g/L of yeast powder, 8-20 g/L of soy peptone, 1.5-2.0 g/L of $MgSO_4 \cdot 7H_2O$, 0.08-0.12 g/L of $MnSO_4 \cdot 5H_2O$, 0.8-1.0 g/L of Tween-80, and a remainder of water; and the pH of the fermenter medium is 7.0;

the inventors found that the viable count of the probiotics in the fermentation broth prepared under the above fermentation conditions was large; and (4) the *Lactobacillus plantarum* C2, *Lactobacillus casei* Zhang, *Lactobacillus plantarum* P8, and *Bifidobacterium animalis* V9 bacterial cells obtained after centrifugation were respectively added with a protectant solution at a mass ratio of respective bacterial cells to the solution of 1:5-10, and mixed uniformly to give bacterial suspensions which were freeze-dried to give *Lactobacillus plantarum* C2 bacteria powder, *Lactobacillus casei* Zhang bacteria powder, *Lactobacillus plantarum* P8 bacteria powder, and *Bifidobacterium animalis* V9 bacteria powder, respectively;

the formulation of the protectant solution was shown as follows (g/L): 30-35 g/L of skim milk powder, 15-20 g/L of desalted whey powder, 15-20 g/L of industrial trehalose, 3-4 g/L of vitamin C, 0.05-0.08 g/L of lecithin, and a remainder of distilled water; the inventors found that the protectant solution with the above composition had a good binding effect with the bacterial cells, and the efficiency of the subsequent freeze-drying process was ensured while the bacterial cells could be well protected.

Preparation of the Composite Probiotic Lactic Acid Bacteria Power:

Components (by weight part): 8 g of *Lactobacillus casei* Zhang bacteria powder, 8 g of *Bifidobacterium animalis* V9 bacteria powder, 6 g of *Lactobacillus plantarum* P8 bacteria powder, 6 g of *Lactobacillus plantarum* C2 bacteria powder, 40 g of galacto-oligosaccharide, 10 g of inulin, and 22 g of blueberry powder;

*Lactobacillus casei* Zhang bacteria powder, *Bifidobacterium animalis* V9 bacteria powder, *Lactobacillus plantarum* P8 bacteria powder and *Lactobacillus plantarum* C2 bacteria powder meeting the following viable count requirements were selected: a viable count of $3.0 \times 10^9$ CFU/g for *Lactobacillus casei* Zhang, a viable count of $4.0 \times 10^9$ CFU/g for *Bifidobacterium animalis* V9, a viable count of $3.0 \times 10^9$ CFU/g for *Lactobacillus plantarum* P8 and a viable count of $1.0 \times 10^9$ CFU/g for *Lactobacillus plantarum* C2;

the bacterial powders of respective weight parts were premixed; and galacto-oligosaccharide, inulin and blueberry powder of the above weight parts were taken and sieved with a 120 mesh sieve, and mixed with the premixed probiotic lactic acid bacteria powder according to the above weight parts; the resultant powder was then sealed into small strip packets, packaged and examined, and packed and transferred into warehouses.

Example 2: Preparation of Composite Probiotic Lactic Acid Bacteria Powder with a Strawberry Flavor Components (by weight part): 6 g of *Lactobacillus casei* Zhang bacteria powder, 5 g of *Bifidobacterium animalis* V9 bacteria powder, 4 g of *Lactobacillus plantarum* P8 bacteria powder, 5 g of *Lactobacillus plantarum* C2 bacteria powder, 50 g of fructo-oligosaccharide, and 30 g of strawberry powder;

*Lactobacillus casei* Zhang bacteria powder, *Bifidobacterium animalis* V9 bacteria powder, *Lactobacillus plantarum* P8 bacteria powder and *Lactobacillus plantarum* C2 bacteria powder meeting the following viable count requirements were selected: a viable count of $5.0 \times 10^9$ CFU/g for *Lactobacillus casei* Zhang, a viable count of $6.0 \times 10^9$ CFU/g for *Bifidobacterium animalis* V9, a viable count of $3.0 \times 10^9$ CFU/g for *Lactobacillus plantarum* P8 and a viable count of $2.0 \times 10^9$ CFU/g for *Lactobacillus plantarum* C2;

the bacterial powders of respective weight parts were premixed; and fructo-oligosaccharide and strawberry powder of the above weight parts were taken and sieved with a 80 mesh sieve, and mixed with the premixed probiotic lactic acid bacteria powder according to the above weight parts; the resultant powder was then sealed into small strip packets, packaged and examined, packed and transferred into warehouses.

For formulations of Examples 1-6, see Table 1.

TABLE 1

Formulation of the composite probiotic lactic acid bacteria powder of each Example

| Components | Weight parts | | | | | |
|---|---|---|---|---|---|---|
| | Example 1 | Example 2 | Example 3 | Example 4 | Example 5 | Example 6 |
| *Lactobacillus plantarum* C2 bacteria powder | 6 | 5 | 4 | 3 | 2 | 1 |
| *Lactobacillus casei* Zhang bacteria powder | 8 | 6 | 2 | 0.5 | 0.2 | 4 |
| *Lactobacillus plantarum* P8 bacteria powder | 6 | 4 | 8 | 5.5 | 3.8 | 1.5 |
| *Bifidobacterium animalis* V9 bacteria powder | 8 | 5 | 6 | 1.2 | 4.5 | 3.5 |
| Prebiotics | Galacto-oligosaccharide, 40; inulin, 10 | Fructo-oligosaccharide, 50 | Fructo-oligosaccharide 15, inulin, 18; polydextrose, 12 | Isomalto-oligosaccharide, 18; soybean oligosaccharide, 12; oligochitosan, 30 | Xylo-oligosaccharide, 19.5; polydextrose, 25; oligolactose, 18 | Fructo-oligosaccharide, 28; oligochitosan, 27 |
| Fruit-vegetable powder | Blueberry powder, 22 | Strawberry powder, 30 | Papaya powder, 10; Hami cantaloupe powder, 15 | Carrot powder, 15; pumpkin powder, 14 | Cranberry powder, 13; pomegranate powder, 14 | Kiwifruit powder, 35 |

Example 7: Effects of Composite Probiotic Lactic Acid Bacteria Powder on the Treatment of Irritable Bowel Syndrome 1. Research Objects 120 patients (aged 18-80, either sex) with IBS who met the Rome III diagnostic criteria and visited gastroenterology department and inpatient department of a hospital were selected as the research objects. Routine examination of blood, urine and stool, examination of liver and kidney function, abdominal ultrasound examination, chest film examination, gastrointestinal endoscopy, and capsule endoscopy were performed on all patients, and no significant organic change was found. Criteria for exclusion: individuals with other gastrointestinal lesions; individuals with dysfunction of heart, liver and kidney; individuals with malignant tumors, diabetes, or previous abdominal surgery; pregnant or lactating women; individuals administrated with drugs (antibiotics, Chinese medicine and the like) which may affect the observation of this study within 4 weeks before the test, individuals with autoimmune diseases and individuals who cannot be reviewed and followed up on time.

2. Experimental Methods 120 patients with IBS were randomly divided into a control group and an experimental group. The control group accepted conventional treatment. The experimental group accepted conventional treatment which was supplemented with the composite probiotic lactic acid bacteria powder. Each group comprised 60 patients. The control group was given the conventional basic treatment. The composite probiotic lactic acid bacteria powder group (i.e., the experimental group) was treated by the conventional basic treatment with the composite probiotic lactic acid bacteria powder which was dissolved in warm water or milk (1 packet, once per day, oral administration after a meal). The above treatment lasted for 28 days.

3. Observed Indicators (1) Stool trait score: stools were divided into seven types according to the Bristol scoring standard. Type 1: hard balls (hard to pass); type 2: sausage-like shape with uneven surface; type 3: sausage-like shape with cracked surface; type 4: sausage- or snake-like shape with a very smooth surface; type 5: soft blocks with smooth broken edge (easy to pass); type 6: fluffy blocks with rough edges, paste-like stool; and type 7: watery stool without solid blocks (complete liquid). Types 1 and 2 indicate constipation, and are scored 2 and 1 respectively; type 3 and type 4 are ideal stools, and are scored 0 point; and types 5 to 7 represent possible diarrhea, and are scored 1, 2 and 3, respectively.

(2) Scores of IBS related symptoms: before and during the treatment, the following items were recorded every day: duration of abdominal pain, duration of abdominal distension, occurrence or absence of abdominal distension and abdominal pain during defecation, proportion of abnormal defecation frequency, proportion of abnormal stool traits, and proportions of mucus stools and tenesmus. According to the scoring criteria of Table 2, the sum of the scores of each symptom was calculated once a week.

TABLE 2

Score table of IBS related symptoms (score)

| Symptom score | 0 | 1 | 2 | 3 |
|---|---|---|---|---|
| Duration of abdominal pain (hours/day) | No | 1-3 | 4-6 | ≥7 |
| Duration of abdominal distention (hours/day) | No | 1-3 | 4-6 | ≥7 |
| Proportion of tenesmus | No | <¼ | ¼-¾ | >¾ |
| Proportion of mucous stool | No | <¼ | ¼-¾ | >¾ |
| Proportion of abnormal stool traits * | No | <¼ | ¼-¾ | >¾ |
| abdominal distension and abdominal pain during defecation | No | <¼ | ¼-¾ | >¾ |
| Proportion of abnormal defecation frequency (day/week) | No | 1-2 | 4-5 | 6-7 |

(3) Judgment criteria of efficacy: Judgment was performed according to a patient's total symptom score and stool trait score. Cure: all symptoms disappeared completely; significantly effective: all symptoms were significantly alleviated (the total symptom score after administration was reduced by more than 50%, as compared with that before administration), and the stool trait score decreased by more than or equal to 2 grades; effective: all symptoms were mildly alleviated (the total symptom score after administration was reduced by 20 to 50%, as compared with that before administration), the stool trait score decreased by 1 grade; and invalid: no significant reduction in symptoms (the total symptom score after administration was reduced by 20%, as compared with that before administration), and the stool trait score did not decrease.

(4) Detection of gut microbiota: The viable counts of *Enterobacter*, *Enterococcus*, *Bacteroides*, *Lactobacillus*, *Bifidobacterium*, and *Clostridium perfringens* in stools were detected.

4. Observation Method (1) The stool traits and symptom scores of the patients of the two groups were recorded on the $0^{th}$, $7^{th}$, $14^{th}$, $21^{st}$, and $28^{th}$ day of the treatment.

(2) The gut microbiota of the patients of the two groups were recorded on the $0^{th}$, $7^{th}$, $14^{th}$, $21^{st}$, and $28^{th}$ day of the treatment.

(3) Differences in the improvement of stool traits and discomfort, treatment efficiency, gut microbiota, and small intestinal bacterial overgrowth were compared between two groups.

5. Treatment Results

The therapeutic effects and cure rates of the control group and the composite probiotic lactic acid bacteria powder group are shown in Table 3. It can be seen that, as compared with the control group, the composite probiotic lactic acid bacteria powder has a very good therapeutic effects on irritable bowel syndrome, and has the characteristics of quick effect and no recurrence.

TABLE 3

Therapeutic effects on patients with IBS and cure rates in the control group and the composite probiotic lactic acid bacteria powder group

| Days of treatment (d) | Control group (60 patients) | | Composite probiotic lactic acid bacteria powder group (60 patients) | |
|---|---|---|---|---|
| | Cure/Significantly effective/effective/invalid | Cure rate (%) | Cure/Significantly effective/effective/invalid | Cure rate (%) |
| 0 | 0/0/0/0 | — | 0/0/0/0 | — |
| 7 | 44/10/5/1 | 73.3 | 52/0/0/0 | 86.7 |
| 14 | 51/7/2/0 | 85.0 | 57/0/0/0 | 95.0 |
| 21 | 58/1/1/0 | 96.7 | 60/0/0/0 | 100.0 |
| 28 | 59/1/0/0 | 98.3 | 60/0/0/0 | 100.0 |

FIG. 1 shows comparison views of Unweighted UniFrac distances and weighted UniFrac distances among samples of the control group and the composite probiotic lactic acid bacteria powder group (referred to as "probiotic bacteria group" for short in FIG. 1). Based on analysis on the Unweighted UniFrac distances, the distance among the samples of the control group increased as the treatment time prolonged. The composite probiotic lactic acid bacteria powder group showed no significant change in the distance among the samples during the whole treatment period, indicating that the composite probiotic lactic acid bacteria powder group (referred to as "probiotic bacteria group" for short in FIG. 1) had relatively small intra-group differences in therapeutic effects. The therapeutic effects of drugs were different on different patients, and thus the control group had relatively large intra-group difference in therapeutic effect. In general, the composite probiotic lactic acid bacteria powder had a more stable therapeutic effect.

Figure 2:
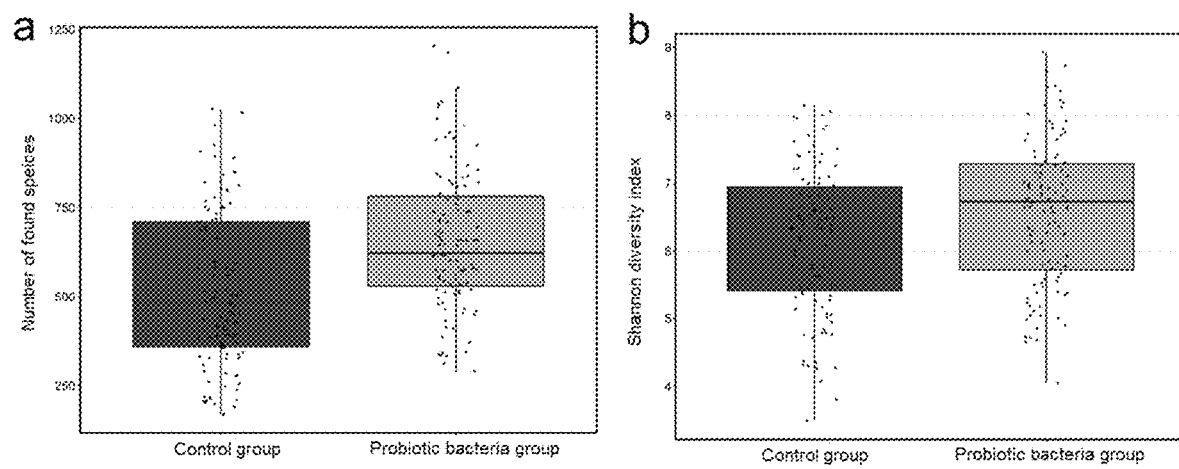
FIG. 2 shows comparison views of species abundance index (Fig. a, P=2.98e-06) and diversity index (Fig. b, P=0.009) of gut microbiota of patients with IBS.

FIG. 2 shows comparison views of species abundance index (Fig. a, P=2.98e-06) and diversity index (Fig. b, P=0.009) of gut microbiota of patients with IBS. By comparing the gut microbiota of the patients, it was found that, as compared with the control group, the species abundance index and the diversity index of the gut microbiota of the patients in the composite probiotic lactic acid bacteria powder group (referred to as "probiotic bacteria group" for short in FIG. 2) were significantly higher than those in the control group. Such results indicates that, as compared with the control group, the treatment supplemented with the composite probiotic lactic acid bacteria powder is more conducive to increase the abundance and diversity of the gut microbiota of the patients, rendering the gut microbiota of the patients healthier and thereby achieving the purpose of treatment being stabilized.

Example 8: Effects of the Composite Probiotic Lactic Acid Bacteria Powder on Treatment of Upper Respiratory Tract Infection Upper respiratory tract infection is referred to as a common cold. Low immunity and exposure to pathogens are the main causes of respiratory tract infection, which is mostly treated with immunomodulators. The upper respiratory tract infection is a general term for acute inflammation of the nasal cavity, pharynx or throat, and it is a most common disease and is the first cause of pediatric outpatient visit and hospitalization. The respiratory tract infection includes upper respiratory tract infection (such as common cold, acute otitis media, tonsillitis, sinusitis, etc.) and lower respiratory tract infection (such as bronchitis, pneumonia, etc.). Recurrent respiratory infection means that upper respiratory tract infection or lower respiratory tract infection occurs frequently within 1 year and the frequency exceeds the normal range. Recurrent respiratory infection is a common problem that plagues patients and physicians, and it is often treated with antibiotics and need hospitalization, and even a surgery is required (such as for otitis media), bringing the patients troubles and economic loss. At present, it is believed that, low immunity of the body is the main cause of recurrent respiratory infection, so it is often advocated that the disease should be prevented and treated with immunomodulators. The immunomodulator generally refers to a drug that can regulate, enhance, excite, and restore the immunity of the body, enhance the immune response of lymphocytes to antigens, increase the levels of IgA and IgG in the body, and thus reduce the frequency of the respiratory infection. Probiotic bacteria can participate in local and systemic immune regulation through a variety of pathways, including increasing colonization resistance, increasing the number and activity of natural killer cells, releasing cytokines, increasing antibody response, and the like. Probiotic bacteria can reduce the frequency of the respiratory infection, reduce severities of symptoms, shorten the course of the disease, and reduce use of antibiotics.

1. Research Objects

A randomized double-blind experiment was performed on 90 young and middle-aged volunteers (20-50 years old, 45 volunteers for each of the composite probiotic lactic acid bacteria powder group (referred to as "probiotic bacteria treatment group" for short) and the placebo group), and 60 elderly volunteers (51 years old or older, 30 volunteers for each of the composite probiotic lactic acid bacteria powder group and the placebo group). All the selected volunteers did not take antibiotics within three months before the experiment and during the experiment.

2. Experimental Method

The young and middle-aged volunteers and the elderly volunteers were randomly divided into the composite probiotic lactic acid bacteria powder group and the placebo group, respectively. Subjects of the composite probiotic lactic acid bacteria powder group ingested 2 g of the composite probiotic lactic acid bacteria powder every day during the experiment. Questionnaires were collected to evaluate the improvement of health status of the volunteers, such as nasal cavity symptoms, oral symptoms, respiratory symptoms, gastrointestinal symptoms, etc. In addition, stool samples on days 0, 180 (6 months) and 360 (12 months) were taken from the volunteers of the composite probiotic lactic acid bacteria powder group and the placebo group for gut microbiota analysis.

3. Treatment Results

Figure 3:
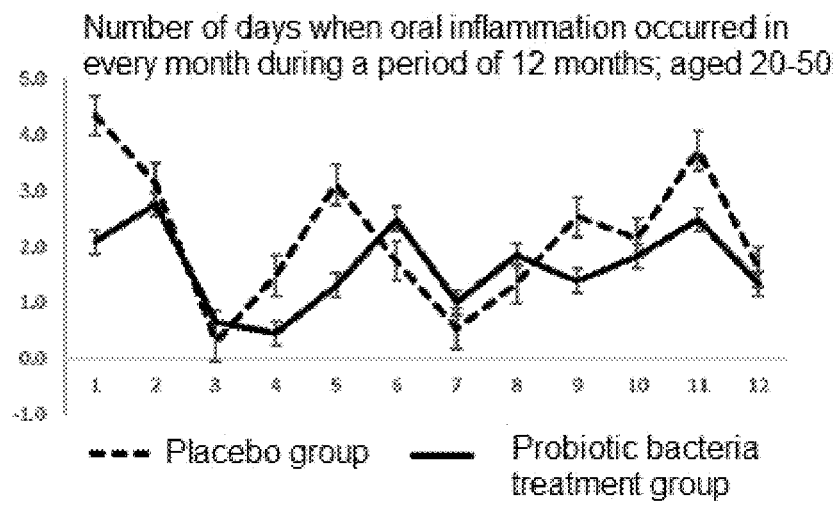
FIG. 3 shows a comparison graph of the occurrence of oral inflammation in every month in volunteers aged 20-50.

FIG. 3 shows a comparison graph of the occurrence of oral inflammation in every month in the volunteers during the period of 12 months. The results show that the occurrences of the oral inflammation in the composite probiotic lactic acid bacteria powder group (referred to as "the probiotic bacteria treatment group" for short in FIGS. 3-10) are significantly lower than that in the placebo group (p<0.05), indicating that intervention with the composite probiotic lactic acid bacteria powder has a protective effect against oral infection.

Figure 4:
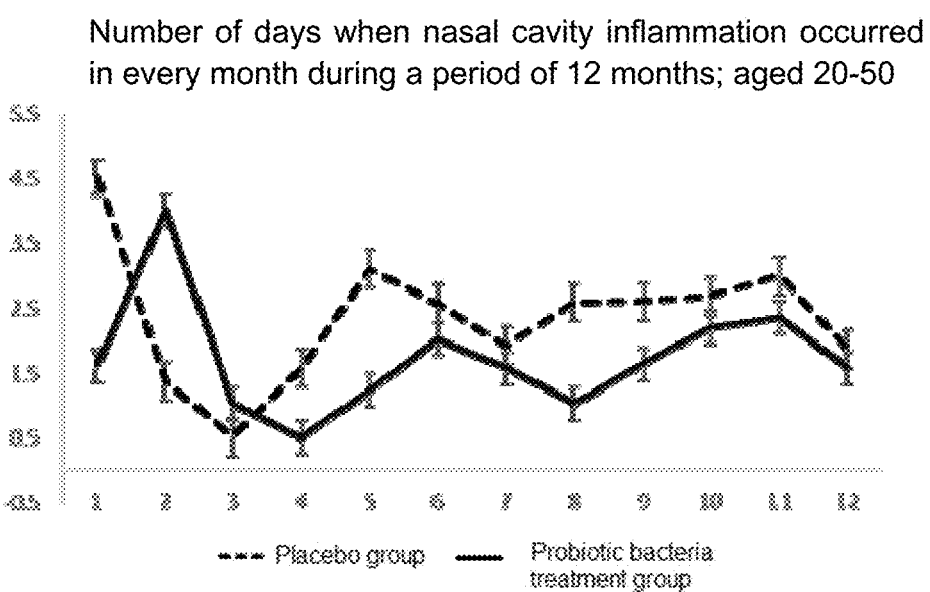
FIG. 4 shows a comparison graph of the occurrence of nasal cavity inflammation in every month in volunteers aged 20-50.
Figure 5:
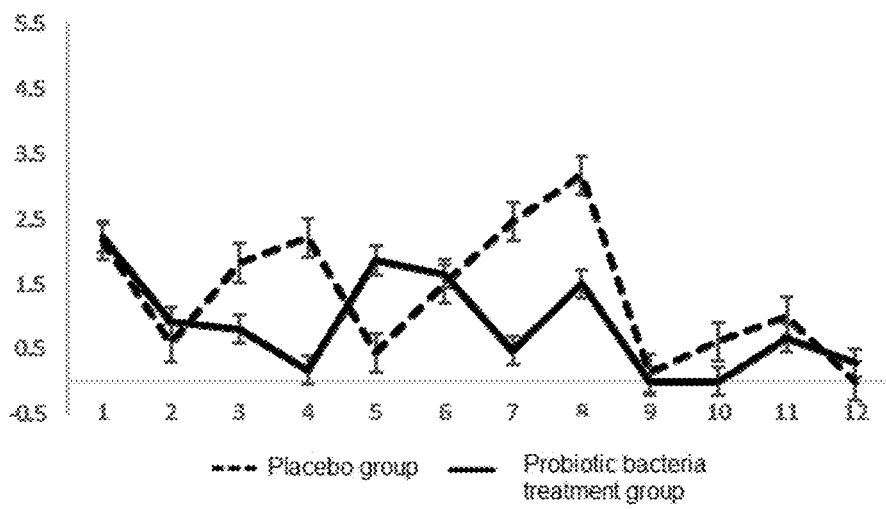
FIG. 5 shows a comparison graph of the occurrence of nasal cavity inflammation in every month in volunteers aged over 50.

FIG. 4 shows a comparison graph of the occurrence of nasal cavity inflammation in every month in the volunteers aged 20-50 during the period of 12 months. FIG. 5 shows a comparison graph of the occurrence of nasal cavity inflammation in every month in the volunteers aged over 50 during the period of 12 months. The results show that the occurrence of the nasal cavity inflammation in the composite probiotic lactic acid bacteria powder group is significantly lower than that in the placebo group (p<0.05), indicating that intervention with the composite probiotic lactic acid bacteria powder has a significantly protective effect against upper nasal cavity infection.

Figure 6:
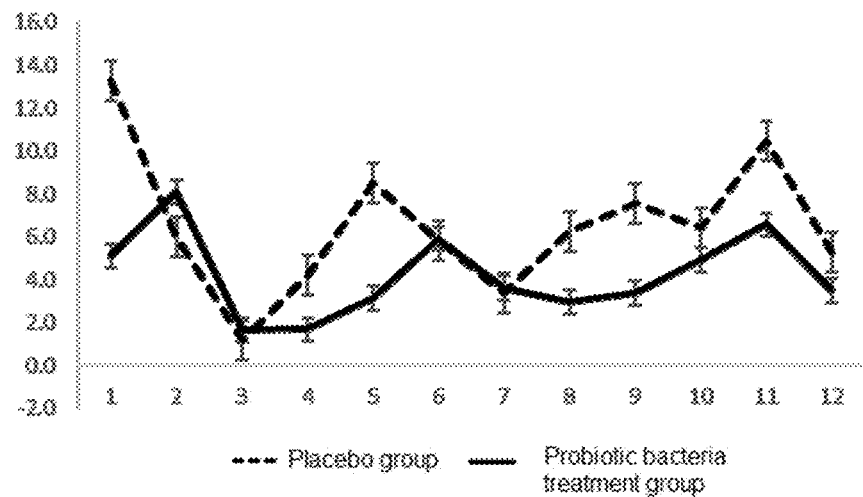
FIG. 6 shows a comparison graph of the occurrence of respiratory inflammation in every month in volunteers aged 20-50.
Figure 7:
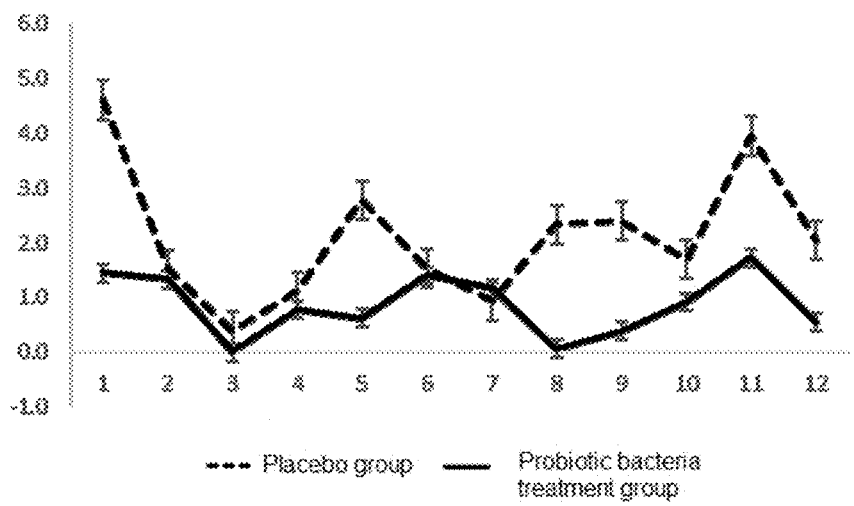
FIG. 7 shows a comparison graph of the occurrence of respiratory inflammation in every month in volunteers aged over 50.

FIG. 6 shows a comparison graph of the occurrence of respiratory inflammation in every month in volunteers aged 20-50 years during the period of 12 months. FIG. 7 shows a comparison graph of the occurrence of respiratory inflammation in every month in the volunteers aged over 50 during the period of 12 months. The results show that both the number of days of respiratory symptom and the occurrence number of flu in the composite probiotic lactic acid bacteria powder group are significantly lower than those in the placebo group (p<0.01), indicating that intervention with the composite probiotic lactic acid bacteria powder has a significantly preventive effect against upper respiratory infection.

Figure 8:
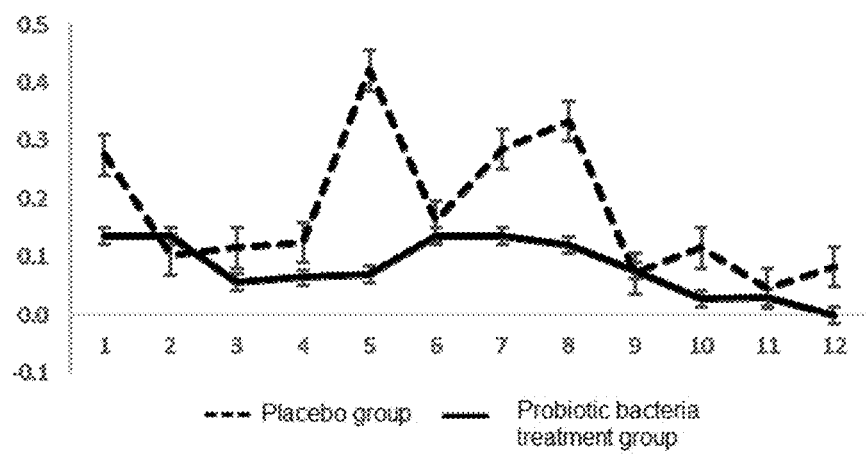
FIG. 8 shows a comparison graph of the occurrence number of diarrhea in every month in volunteers aged 20-50.
Figure 9:
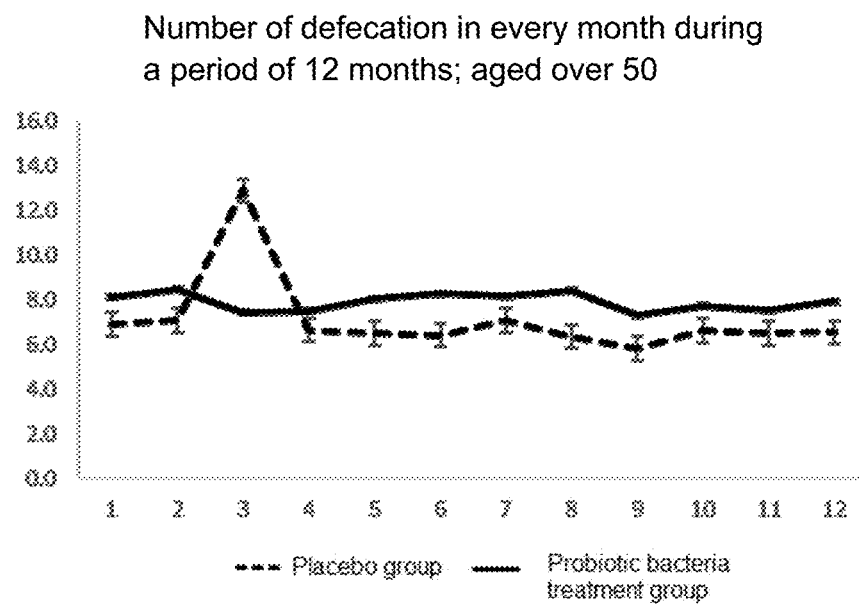
FIG. 9 shows a comparison graph of the number of defecation in every month in volunteers aged over 50.

FIG. 8 shows a comparison graph of the occurrence number of diarrhea in every month in the volunteers aged 20-50 years during the period of 12 months. FIG. 9 shows a comparison graph of the occurrence number of defecation in every month in volunteers aged over 50 during the period of 12 months. The results show that the occurrence number of diarrhea in the composite probiotic lactic acid bacteria powder group shows a significant decreasing trend as compared with the placebo group (p=0.079, close to 0.05). The number of defecation per week in the elderly intervention group with the composite probiotic lactic acid bacteria powder was significantly increased as compared with the placebo group (p<0.05), indicating that intervention with the composite probiotic lactic acid bacteria powder can improve the frequency of defecation in the elderly population.

Figure 10:
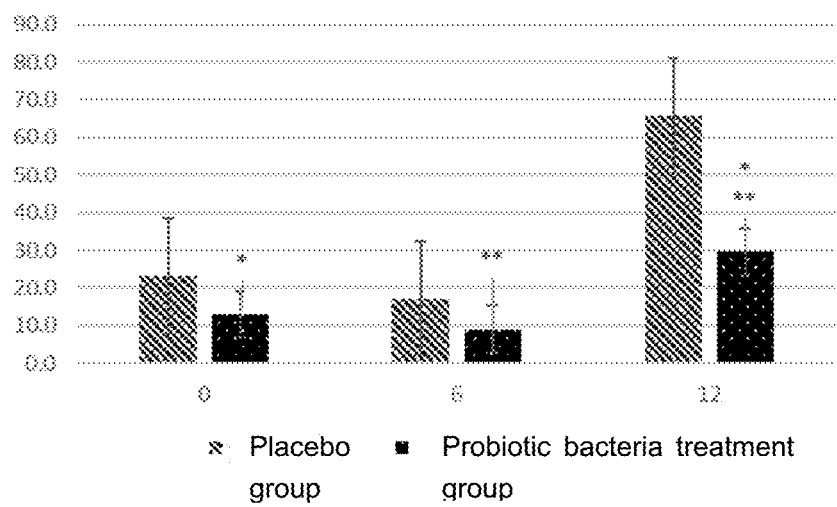
FIG. 10 shows a comparison view of immunoglobulin IgG contents in blood samples of volunteers aged 20-50.

FIG. 10 shows a comparison view of immunoglobulin IgG contents in blood samples of the volunteers aged 20-50 during the period of 12 months. Immunoglobulin IgG is a main type of antibody found in blood and cytolymph, accounting for 75% of total human serum antibodies, and is used to control tissue infection. IgG is produced and secreted by B cells and plays a role in anti-infection through binding with a variety of pathogenic bacteria. The intervention in the composite probiotic lactic acid bacteria powder group significantly increased the blood IgG level in the young and middle-aged volunteers (p<0.01), indicating that the composite probiotic lactic acid bacteria powder can increase the immunity of young and middle-aged people.

TABLE 4

Bacteria species changed in the elderly group after intake of the composite probiotic lactic acid bacteria powder for 12 months

| Species | Month 0 | Month 12 | Wilcoxon.test | Month 12 VS Month 0 |
|---|---|---|---|---|
| *Eubacterium hallii* | 0.51 ± 0.09 | 0.04 ± 0.02 | 0.00023584 | ↓ |
| *Blautia wexlerae* | 0.57 ± 0.16 | 0.09 ± 0.03 | 0.000379127 | ↓ |
| *Parabacteroides distasonis* | 0.38 ± 0.09 | 0.99 ± 0.28 | 0.041250017 | ↑ |

It can be seen from Table 4 that, after intake of the composite probiotic lactic acid bacteria powder for 12 months, the gut microbiota of the elderly group was significantly changed. The relative contents of *Eubacterium hallii* and *Blautia wexlerae* decreased significantly, and the relative content of *Parabacteroides distasonis* increased significantly, indicating that the composite probiotic lactic acid bacteria powder can contribute to juvenescence of the gut microbiota in elderly volunteers. During the intervention with the composite probiotic lactic acid bacteria powder, the composite probiotic lactic acid bacteria powder could continuously increase the species abundance and diversity of the gut microbiota of the volunteers, and promote the stability of the gut microbiota diversity of the volunteers, so that the gut microbiota diversity may not be changed greatly with seasons, diets, and the like.

In summary, the composite probiotic lactic acid powder composited from *Lactobacillus casei* Zhang, *Bifidobacterium animalis* V9, *Lactobacillus plantarum* P8, and *Lactobacillus plantarum* C2 has many probiotic effects: effectively treating irritable bowel syndrome and reducing recurrence thereof; having a significantly protective effect against oral infection and nasal cavity infection, having a significantly preventive effect against upper respiratory tract infection; and at the same time, improving gastrointestinal symptoms, regulating gut microbiota, reducing the age index of the gut microbiota, and causing the trend of juvenescence in the gut microbiota of the elderly people; and increasing the level of IgG in blood and improve the body immunity.

*Lactobacillus plantarum* C2 is further described below.

*Lactobacillus plantarum* C2 strain is a lactic acid bacteria strain with good probiotic characteristics, which was isolated and screened from naturally fermented pickle in Sichuan Province (China) in 2012. Acids can be quickly produced in the crops or animal wastes fermented by the strain so as to control the pH value of the materials, in which there is a high-yield organic acid, 4-hydroxyphenyl lactic acid, which has broad-spectrum inhibition effect on the growth and reproduction of *Escherichia coli* pathogens and moulds. This organic acid was first discovered by the team of the invention and has high research potential.

*Lactobacillus plantarum* C2 is Gram-positive, sporeless and straight-bar bacteria (1.2 vtm*6.2 μm), which has no flagella, and it is movable and facultative anaerobic. The surface colony of *Lactobacillus plantarum* C2 is circular with a diameter of about 2.5 mm and is convex with a smooth surface, also it is dense and white. This strain can grow and reproduce at 20° C., and the optimum growth temperature range is 35 to 37° C. This strain has good acid resistance and bile salt resistance, and its survival rate is up to 82.42% after digestion in artificial simulated gastric juice at pH 2.5 for 3 hours followed by digestion in artificial intestinal juice at pH 8.0 for 8 hours.

This strain was deposited on Aug. 18, 2017 at the China General Microbiological Culture Collection Center (CGMCC), the accession number is CGMCC No. 14532, the address of the CGMCC is Institute of Microbiology, Chinese Academy of Sciences, No. 1 West Beichen Road, Chaoyang District, Beijing, 100101, China, and this strain is classified as *Lactobacillus plantarum*.

Determination of the Acid Resistance and Bile Salt Resistance and Bacterial Inhibition Activity of *Lactobacillus plantarum* C2

The cryopreserved *Lactobacillus plantarum* C2 was inoculated to MRS liquid medium, cultured in a static state at 37° C. for 18 hours. The *Lactobacillus plantarum* C2 was subcultured twice to give an activated fermentation broth.

The composition of the MRS liquid medium was shown as follows (g/L): 10 g/L of peptone, 5 g/L of beef extract, 4 g/L of yeast extract powder, 20 g/L of glucose, 2 g/L of dipotassium hydrogen phosphate, 5 g/L of sodium acetate, 2 g/L of trisodium citrate, 1 mL of tween −80, 0.2 g/L of magnesium sulfate, and 0.05 g/L of manganese sulfate were added to 1000 mL of distilled water, and the pH was adjusted to 6.5. The obtained medium was sterilized at 121° C. for 15 minutes.

1. Determination of the Acid Resistance and Bile Salt Resistance 3.5 g/L pepsin was added to a sterilized PBS buffer at pH 2.5 (adjusted with 1 mol/L HCl), and the resultant solution was subjected to filtration sterilization with a 0.22 μm microporous membrane to prepare a simulated gastric juice. The activated fermentation broth was centrifuged to collect bacterial cells, and the cells were added to the simulated gastric juice at pH 2.5 in an amount equal to that of the medium and cultured at 37° C. for 3 hours. At the $0^{th}$ hour and the $3^{rd}$ hour, the viable counts were determined by the pouring method using MRS agar medium.

0.1% of trypsin and 1.8% of bovine bile salt were added to a sterilized PBS buffer at pH 8.0 (which was adjusted with 0.1 mol/L NaOH), and the resultant solution was subjected to filtration sterilization with a 0.22 μm microporous membrane to prepare a simulated intestinal juice. The bacterial fluid, after treatment with the simulated gastric juice for 3 hours, was subjected to centrifugation and washing twice to collect bacterial cells, and the cells were added to the simulated intestinal juice in an amount equal to that of the simulated gastric juice and cultured at 37° C. At the $4^{th}$ hour and the $8^{th}$ hour, the viable counts were determined by the pouring method using MRS agar medium. The experimental results are shown in Table 5.

Survival rate=$[N_1/N_0]\times 100\%$ ($N_0$–viable count at the $0^{th}$ hour;$N1$–viable count after digestion with simulated intestinal and gastric juice)

TABLE 5

Survival rate of *Lactobacillus plantarum* C2 in artificial simulated gastric and intestinal juice

| | Artificial simulated gastric juice at pH 2.5 (1 g CFU/mL) | | Survival rate (%) | Artificial simulated Intestinal juice at pH 8.0 (1 g CFU/mL) | | Survival rate after 4 hours (%) | Survival rate after 8 hours (%) |
|---|---|---|---|---|---|---|---|
| Strain | 0 (hour) | 3 (hours) | | 4 (hours) | 8 (hours) | | |
| C2 | 9.50 ± 0.08 | 8.34 ± 0.05 | 87.79 | 8.11 ± 0.09 | 7.83 ± 0.14 | 85.37 | 82.42 |

2. Determination of Bacterial Inhibition Activity

The bacterial inhibition activity effect of *Lactobacillus plantarum* C2 fermentation broth was determined through Well-diffusion Agar Assay: after sterilization, MRS agar medium (20 ml) was cooled to about 50° C. and poured into a plate together with 200 μL of intestinal pathogenic bacteria solution ($10^6$ cfu/ml), and then mixed well. After cooling and solidification of the MRS agar medium containing the intestinal pathogenic bacteria, wells with a diameter of about 8 mm were made on the plate using a puncher.

100 µL of *Lactobacillus plantarum* C2 fermentation broth was added to each well, and after diffusion for 12 hours in a refrigerator at 4° C., and the plate was cultured at 37° C. for 48 hours. Then the size of an inhibition zone was observed. The diameter of the inhibition zone was measured using a vernier caliper (two significant figures were retained) and the results are shown in Table 6:

TABLE 6

Phenyllactic acid and 4-hydroxyphenyl lactic acid contents and bacterial inhibition activity of *Lactobacillus plantarum* fermentation broth

| Item | Measurement result |
| --- | --- |
| Phenyllactic acid (mg/L) | 56.25 ± 0.98 |
| 4-hydroxyphenyl lactic acid (mg/L) | 20.76 ± 1.35 |
| *Escherichia coli* 0517: H7 (mm) | 42.50 ± 1.18 |
| *Salmonella typhimurium* (mm) | 16.88 ± 1.49 |
| *Shigella flexneri* (mm) | 17.57 ± 1.84 |
| *Staphylococcus aureus* (mm) | 29.27 ± 1.07 |

Note:
the puncher has a diameter of 8 mm.

It can be seen from the experimental results in Table 5 and Table 6 that, the *Lactobacillus plantarum* C2 strain has relatively good acid and bile salt resistance, and its survival rate is up to 82.42% after digestion in artificial simulated gastric juice at pH 2.5 for 3 hours followed by digestion in artificial intestinal juice at pH 8.0 for 8 hours. At the same time, the C2 strain has an excellent characteristic of broad-spectrum inhibition of pathogenic bacteria, and the bacterial inhibition effect is very significant.

The application has been described in detail above with reference to the specific embodiments and exemplary examples, but these are not to be construed as limiting on the invention(s). It will be understood by those skilled in the art that various equivalent replacements, modifications, and improvements may be made without departing from the spirit and scope of the invention, all of which will fall within the scope of the invention(s). The protection scope of the invention(s) is defined by the appended claims.

What is claimed is:

1. A composite probiotic lactic acid bacteria powder for treating irritable bowel syndrome and upper respiratory tract infection, oral infection, or nasal cavity infection, comprising *Lactobacillus plantarum* C2 with an accession number of CGMCC No. 14532, *Lactobacillus casei* Zhang with an accession number of CGMCC No. 5469, *Lactobacillus plantarum* P8 with an accession number of CGMCC No. 6312 and *Bifidobacterium animalis* V9 with an accession number of CGMCC No. 5470,
    wherein, an effective viable count of *Lactobacillus plantarum* C2 is greater than or equal to $1.0 \times 10^9$ CFU/g, an effective viable count of *Lactobacillus casei* Zhang is greater than or equal to $3.0 \times 10^9$ CFU/g, an effective viable count of *Lactobacillus plantarum* P8 is greater than or equal to $3.0 \times 10^9$ CFU/g, and an effective viable count of *Bifidobacterium animalis* V9 is greater than or equal to $4.0 \times 10^9$ CFU/g.

2. The composite probiotic lactic acid bacteria powder of claim 1, wherein a total effective viable count of the composite probiotic lactic acid bacteria powder is greater than or equal to $1 \times 10^{10}$ CFU/g.

3. The composite probiotic lactic acid bacteria powder of claim 1, further comprising prebiotics and/or fruit-vegetable powder, wherein the prebiotics comprise one or more of fructo-oligosaccharide, galacto-oligosaccharide, xylo-oligosaccharide, isomalto-oligosaccharide, oligolactose, oligochitosan, soybean oligosaccharide, inulin, and polydextrose; and the fruit-vegetable powder comprises one or more of blueberry powder, strawberry powder, cranberry powder, cherry powder, apple powder, banana powder, papaya powder, mango powder, pitaya powder, pumpkin powder, carrot powder, grape powder, pomegranate powder, Hami cantaloupe powder, Chinese wolfberry powder, red jujube powder, and kiwifruit powder.

4. The composite probiotic lactic acid bacteria powder of claim 1, comprising 1-6 parts by weight of *Lactobacillus plantarum* C2 bacteria powder, 0.1-8 parts by weight of *Lactobacillus casei* Zhang bacteria powder, 0.1-6 parts by weight of *Lactobacillus plantarum* P8 bacteria powder, 0.1-8 parts by weight of *Bifidobacterium animalis* V9 bacteria powder, 30-75 parts by weight of prebiotics, and 5-35 parts by weight of fruit-vegetable powder.

5. The composite probiotic lactic acid bacteria powder of claim 3, wherein the composite probiotic lactic acid bacteria powder has a moisture content of not more than 2%.

6. A method of using the composite probiotic lactic acid bacteria powder of claim 1 in the preparation of a product for treating irritable bowel syndrome, upper respiratory tract infection, oral infection, and nasal cavity infection.

7. A method of using the composite probiotic lactic acid bacteria powder of claim 2 in the preparation of a product for treating irritable bowel syndrome, upper respiratory tract infection, oral infection, and nasal cavity infection.

8. A method of using the composite probiotic lactic acid bacteria powder of claim 3 in the preparation of a product for treating irritable bowel syndrome, upper respiratory tract infection, oral infection, and nasal cavity infection.

9. A method of using the composite probiotic lactic acid bacteria powder of claim 4 in the preparation of a product for treating irritable bowel syndrome, upper respiratory tract infection, oral infection, and nasal cavity infection.

10. A method of using the composite probiotic lactic acid bacteria powder of claim 5 in the preparation of a product for treating irritable bowel syndrome, upper respiratory tract infection, oral infection, and nasal cavity infection.

11. The composite probiotic lactic acid bacteria powder of claim 2, wherein the total effective viable count of the composite probiotic lactic acid bacteria powder is equal to or greater than $1.6 \times 10^{10}$ CFU/g.

* * * * *